United States Patent
Wang et al.

(10) Patent No.: US 11,458,180 B2
(45) Date of Patent: Oct. 4, 2022

(54) ENVIRONMENTALLY-FRIENDLY PREPARATION METHOD OF COMPOSITION CONTAINING ANTI-INFLAMMATORY ACTIVE INGREDIENTS AND USE OF COMPOSITION

(71) Applicant: SHANGHAI JAKA BIOTECH CO., LTD., Shanghai (CN)

(72) Inventors: Xinliang Wang, Shanghai (CN); Yina Lu, Shanghai (CN); Jun Tian, Shanghai (CN)

(73) Assignee: SHANGHAI JAKA BIOTECH CO., LTD., Shanghai (CN)

( * ) Notice: Subject to any disclaimer, the term of this patent is extended or adjusted under 35 U.S.C. 154(b) by 1 day.

(21) Appl. No.: 17/280,069

(22) PCT Filed: Oct. 12, 2020

(86) PCT No.: PCT/CN2020/120294
§ 371 (c)(1),
(2) Date: Mar. 25, 2021

(87) PCT Pub. No.: WO2021/082889
PCT Pub. Date: May 6, 2021

(65) Prior Publication Data
US 2022/0000956 A1 Jan. 6, 2022

(30) Foreign Application Priority Data

Oct. 30, 2019 (CN) .......................... 201911045380.X

(51) Int. Cl.
| A61K 36/539 | (2006.01) |
| A61P 29/00 | (2006.01) |
| A61K 36/484 | (2006.01) |
| A61K 36/489 | (2006.01) |

(52) U.S. Cl.
CPC .......... *A61K 36/539* (2013.01); *A61K 36/484* (2013.01); *A61K 36/489* (2013.01); *A61P 29/00* (2018.01); *A61K 2236/331* (2013.01); *A61K 2236/37* (2013.01); *A61K 2236/53* (2013.01)

(58) Field of Classification Search
CPC combination set(s) only.
See application file for complete search history.

(56) References Cited

U.S. PATENT DOCUMENTS

2009/0053339 A1* 2/2009 Cohen ..................... A61P 25/06
424/773

* cited by examiner

*Primary Examiner* — Aaron J Kosar
(74) *Attorney, Agent, or Firm* — Bayramoglu Law Offices LLC

(57) ABSTRACT

An environmentally-friendly preparation method of a composition containing anti-inflammatory ingredients and use of the composition are provided. The method includes: S1. weighing a specified volume of water and adjusting the pH, adding *Sophora flavescens* roots, and subjecting a resulting mixture to extraction at a high temperature; S2. adjusting pH of an obtained solution in step S1, adding *Glycyrrhiza inflata* roots, and heating a resulting mixture to boiling for extraction; S3. adding *Scutellaria baicalensis* roots to an obtained boiling solution from the extraction in step S2, and subjecting a resulting mixture to extraction, filtration, and pH adjustment; S4. adding activated carbon to an obtained filtrate in step S3, and subjecting a resulting mixture to incubation and filtration; S5. adding a clarifying agent to an obtained filtrate in step S4, and subjecting a resulting mixture to standing and filtration; and S6. subjecting an obtained filtrate in step S5 to membrane separation.

10 Claims, 1 Drawing Sheet

ENVIRONMENTALLY-FRIENDLY PREPARATION METHOD OF COMPOSITION CONTAINING ANTI-INFLAMMATORY ACTIVE INGREDIENTS AND USE OF COMPOSITION

CROSS REFERENCE TO THE RELATED APPLICATIONS

This application is the national phase entry of International Application No. PCT/CN2020/120294, filed on Oct. 12, 2020, which is based upon and claims priority to Chinese Patent Application No. 201911045380.X, filed on Oct. 30, 2019, the entire contents of which are incorporated herein by reference.

TECHNICAL FIELD

The present invention relates to the technical field of biomedicine and cosmetics, and in particular to an environmentally-friendly preparation method of a composition containing anti-inflammatory active ingredients and use of the composition.

BACKGROUND

*Scutellaria baicalensis* has long been used for diseases such as seasonal febrile disease, pneumonia, abscesses, and furunculosis due to its effects of clearing away pathogenic heat and dampness, purging intense heat, and detoxification. *Sophora flavescens* has the functions of clearing away pathogenic heat and dampness, killing insects, and promoting urination, and is used for eczema, pruritus, and so on. *Glycyrrhiza* has the effects of clearing away heat and toxic materials, expelling phlegm and subdue coughing, spasm and pain relief, and reconciling various medicines. Glycyrrhizic acid shows antagonism to many links such as the occurrence, development, and response of inflammation. However, different extraction methods may result in different compositions of active ingredients, which may lead to different effects. Traditionally, the three medicines require to be co-decocted just before administration, which is troublesome, unfavourable for long-term storage, and inconvenient for use.

There have been a large number of reports on the extraction and purification process for the main active ingredients in each of *Sophora flavescens, Scutellaria baicalensis*, and *Glycyrrhiza*. The main methods include water extraction, alcohol extraction, and the like. However, for large-scale production, ethanol is a Class A dangerous article and needs to be stored in a warehouse designed as a Class A fireproof building at an amount that should not be large. Therefore, in a production process, less or no ethanol should be used in consideration of environmental protection and economy. The water extraction method has low efficiency and is prone to deterioration and bacterium growth in a high temperature environment. In large-scale production, it is necessary to consider shortening a process, improving efficiency, saving energy, and protecting the environment.

There are no detailed reports in patents on the extraction of active ingredients simultaneously from any two of *Sophora flavescens, Scutellaria baicalensis*, and *Glycyrrhiza*, as well as few related reports in literatures.

For example, Chinese patent CN2016109373139 "Traditional Chinese Medicine Extract Composition with Anti-skin Irritation Effect and Preparation Method Thereof" discloses a method for subjecting *Glycyrrhiza, Sophora flavescens, Scutellaria baicalensis, Angelica sinensis, Ligusticum wallichii, Herba Schizonepetae, Radix Saposhnikoviae*, and White Willow Bark to ethanol extraction, which is different from an aqueous extraction method where medicinal materials are fed in a specified order according to the properties of active substances in each medicinal material.

For example, in literature 1 ((Lu Bing, Yang Xuan, Wang Baohua, et al. Research on solubilization of glycyrrhizic acid on baicalin [J]. Journal of Beijing University of Traditional Chinese Medicine, 2014, 37 (9): 620-624.), a method for subjecting *Glycyrrhiza* and *Scutellaria baicalensis* to heat reflux co-extraction with water to increase a yield of baicalin, with a glycyrrhizic acid yield of 0.22 g/L and a baicalin yield of 164 mg/38 ml.

In literature 2 (Zhao Yang, Zhang Tao, Jia Hongmei, et al. Optimization of Extraction Process for Medicine Pair of *Sophora flavescens-Glycyrrhiza* and Analysis of Chemical Components therefrom [J]. Chinese Journal of Experimental Traditional Medical Formulae, 2017 (03): 26-32.), a method for increasing the yields of *Sophora flavescens* total alkali and glycyrrhizic acid is provided, where, *Glycyrrhiza* and *Sophora flavescens* are mixed at a ratio of 1:1 and subjected to reflux co-extraction with 60% ethanol.

In literature 3 (Liu Bin, Shi Renbing, Zhu Lijun, et al. Study on HPLC fingerprint of flavonoids in *Sophora flavescens* Decoction and Correlation of HPLC fingerprint with *Scutellaria baicalensis* and *Sophora flavescens* in Formula [J]. China Journal of Chinese Materia Medica, 2007, 32 (16): 1631-1634.), a method for subjecting a mixture of *Sophora flavescens-Scutellaria baicalensis-Radix Rehmanniae* (3:2:8) to reflux co-extraction with 70% ethanol and studying corresponding fingerprints is provided, but no experiment is conducted to illustrate a relationship between extracted biologically active ingredients and drug effects.

However, the above works of literature do not involve a method for subjecting the three medicinal materials of *Sophora flavescens, Scutellaria baicalensis*, and *Glycyrrhiza* to co-extraction with an aqueous solution, which has a simplified process and reduced steps, has a reduced contamination risk, and can achieve energy conservation and environmental protection. In addition, in the above works of literature, no specific solutions are proposed specifically for the stability of solvents, devices, solution products that require attention in large-scale production and for the efficacy changes caused by process changes.

SUMMARY

In view of the shortcomings in the prior art, the present invention is intended to provide an environmentally-friendly preparation method of a composition containing anti-inflammatory active ingredients. Specifically, in preparation, three medicinal materials of *Sophora flavescens* roots, *Scutellaria baicalensis* roots, and *Glycyrrhiza inflata* roots are fed in a specified order for co-extracting biologically active ingredients, so as to achieve the following effects:

1) The present invention has a simplified process and no organic solvents, results in no wastewater and a reduced contamination risk, and is energy-saving as well as environmentally-friendly.

2) Moreover, through the improvement of a process involved in the present invention, the application of a product in biomedicines, food and health products, and cosmetics can be expanded, especially, the effect on skin can be enhanced and expanded.

The objectives of the present invention are achieved by the following technical solutions.

The present invention provides an environmentally-friendly preparation method of a composition containing anti-inflammatory active ingredients, including the following steps:

S1. weighing a specified volume of water and adjusting pH, adding *Sophora flavescens* roots, and subjecting a resulting mixture to extraction at a high temperature;

S2. adjusting pH of an obtained solution from the extraction in step S1, adding *Glycyrrhiza inflata* roots, and heating a resulting mixture to boiling for extraction;

S3. adding *Scutellaria baicalensis* roots to an obtained boiling solution from the extraction in step S2, and subjecting a resulting mixture to extraction, filtration, and pH adjustment;

S4. adding activated carbon to an obtained filtrate in step S3, and subjecting a resulting mixture to incubation and filtration;

S5. adding a clarifying agent to an obtained filtrate in step S4, and subjecting a resulting mixture to standing and filtration; and S6. subjecting an obtained filtrate in step S5 to membrane separation to obtain the composition containing anti-inflammatory active ingredients.

Preferably, the *Scutellaria baicalensis* roots, *Sophora flavescens* roots, and *Glycyrrhiza inflata* roots may be added at a ratio of (21-40):(21-40):(21-40). Within the material ratio range, the composition containing anti-inflammatory active ingredients can be obtained.

In the present invention, *Glycyrrhiza inflata* roots are specifically selected for compound extraction with *Scutellaria baicalensis* roots and *Sophora flavescens* roots, which can achieve a superior anti-inflammatory effect and lead to a final product with high stability. However, if other licorice roots such as *Glycyrrhiza uralensis* roots or *Glycyrrhiza glabra* roots are selected for compound extraction with *Scutellaria baicalensis* roots and *Sophora flavescens* roots, an obtained composition exhibits an anti-inflammatory effect inferior to that of the present invention, and ingredients in the licorice roots will negatively affect the color, appearance, and stability of a final product.

Preferably, in step S1, the water may be added at an amount 5 to 10 times the total amount of medicinal materials; the pH may be 3.0 to 7.0; and the high-temperature extraction may be conducted at 60° C. to 80° C. for 30 min to 2 h.

Preferably, in step S2, the pH may be adjusted to 8 to 10 with 1% to 10% NaOH, and the boiling solution may be subjected to extraction for 30 min to 2 h. The slightly alkaline condition resulting from matrine is conducive to the dissolution of glycyrrhizic acid, and the surface activity of glycyrrhizic acid is conducive to the dissolution of matrine. Moreover, with a slightly alkaline pH, matrine is not destroyed and glycyrrhizic acid is in an ionic state, which is more conducive to the dissolution of glycyrrhizic acid and other active ingredients.

Preferably, in step S3, the extraction may be conducted for 30 min to 2 h, and the pH may be adjusted to 5.5 to 7.5.

In this step, the *Scutellaria baicalensis* roots include special baicalinase, which tends to hydrolyze baicalin, causing the reduction of baicalin. Therefore, it is necessary to use boiling to inactivate baicalinase, thus retaining the component of baicalin and enhancing the efficacy. In addition, baicalin is a flavonoid compound with multiple phenolic hydroxyl groups, and plant cell walls are easily ruptured at a pH of 8 to 10, thus increasing the dissolution of flavonoids in *Scutellaria baicalensis* roots. Under alkaline conditions, matrine can form hydrogen bonds with baicalin to enhance the solubility of baicalin. Moreover, glycyrrhizic acid can increase a surface tension of a solution, which improves the extraction efficiency of matrine and baicalin.

In the present invention, it is found through preliminary tests:

1. In a traditional method for co-decocting the three medicinal materials, *Scutellaria baicalensis* roots, *Sophora flavescens* roots, and *Glycyrrhiza inflata* roots are fed at the same time, then water extraction is conducted, pH of a resulting filtrate is adjusted to 5.5 to 7.5, and then the filtrate is subjected to the treatments of steps S4 to S6. Experimental results show that filtration is difficult in the process, causing difficulties in a production process.

2. In a case where the three materials are added in a changed order, for example:

A. Water is added and pH is adjusted to 8 to 10 with 10% NaOH; *Glycyrrhiza inflata* roots are first added for extraction, then *Sophora flavescens* roots are added for extraction, and finally *Scutellaria baicalensis* roots are added for extraction; a resulting solution is filtered to obtain a filtrate and pH of the filtrate is adjusted to 5.5 to 7.5; and then the filtrate is subjected to the treatments of steps S4 to S6. Under slightly alkaline conditions, matrine is in a free state and has insufficient water solubility, and the present invention adopts water extraction from the perspective of environmental protection, so a content of the active ingredient matrine in a water extraction solution is reduced. Compared with the process of the present invention, an extraction yield of matrine is reduced by 32.3%.

Provided that after *Glycyrrhiza inflata* roots are subjected to extraction, pH of a resulting solution is first adjusted to acidity and then *Sophora flavescens* roots are subjected to extraction, an extraction yield of matrine can be kept unchanged, but the acidic environment and the heating condition during the extraction process will promote the acid hydrolysis of glycyrrhizic acid to form glycyrrhetinic acid, which reduces an actual content of glycyrrhizic acid in a product by 18.7%.

B. Water is added, *Scutellaria baicalensis* roots are first added for extraction, and *Sophora flavescens* roots are then added for extraction; pH of a resulting solution is adjusted to 8 to 10 with 10% NaOH, and *Glycyrrhiza inflata* roots are added for extraction; a resulting solution is filtered to obtain a filtrate and pH of the filtrate is adjusted to 5.5 to 7.5; and then the filtrate is subjected to the treatments of steps S4 to S6. This solution will also lead to reduction in a content of the active ingredient baicalin. As baicalin has extremely poor water solubility, a strong alkaline condition is a must to achieve a high dissolution rate of baicalin. Furthermore, according to the aforementioned literature 1, a solubilizing effect of glycyrrhizic acid on baicalin cannot be exerted. Compared with the process of the present invention, an extraction yield of baicalin is reduced by 21.4%.

C. Water is added, *Sophora flavescens* roots are first added for extraction to obtain a *Sophora flavescens* root extraction solution, and then 10% NaOH is added to adjust a pH to 9; *Glycyrrhiza inflata* roots and *Scutellaria baicalensis* roots are added, a resulting mixture is heated to boiling, and extraction is conducted; a resulting solution is filtered to obtain a filtrate and pH of the filtrate is adjusted to 5.5 to 7.5; and then the filtrate is subjected to the treatments of steps S4 to S6. This solution will also lead to a decrease of 36.1% in a content of the active ingredient baicalin. On the surface, both glycyrrhizic acid and baicalin require alkaline conditions to be dissolved at a high rate, which seems plausible.

In fact, the long-time stay in alkaline boiling water will promote the ring-opening variation of a C-ring structure of baicalin, thereby greatly reducing an actual content of baicalin.

Therefore, if the three raw materials are added in a changed order, extraction yields of the main active ingredients in the medicinal materials will be significantly reduced, which will ultimately reduce contents of key active ingredients in a prepared composition and thus affect the efficacy of the composition; and contents of inactive ingredients will be increased, which will lead to the increase of side effects.

Preferably, in step S4, the activated carbon may be added at an amount 0.2% to 1% of the total amount of the filtrate; and the incubation may be conducted at 85° C. to 95° C. for 0.5 h to 1 h.

In the above step, a resulting solution has a dark color, and activated carbon is used to remove part of pigments.

Preferably, in step S5, the clarifying agent may be one of chitosan, ZTC clarifying agent I-IV, and 101 juice clarifying agent, or a combination of two or more thereof, the clarifying agent may be added at an amount 1% to 5% of the total amount of the filtrate; and the standing may last for 0.5 h to 1 h.

In the above step, water is used as an extraction solvent. During water extraction, in addition to small-molecule biologically active ingredients, a large number of water-soluble impurities in plants such as sugars and proteins are also easily extracted, resulting in low content of biologically active molecules. Moreover, sugars, proteins, etc. are prone to breed bacteria, and so a composition is easily deteriorated after long-term storage. In the present invention, a clarifying agent is used to remove impurities prone to breed bacteria, so that a composition has a reduced risk of bacterium growth and biologically active ingredients have increased contents and enhanced activities.

The membrane separation may include the following: separating with a microfiltration membrane; separating with an ultrafiltration membrane; and desalting with a reverse osmosis (RO) membrane.

Preferably, the method may further include the step of subjecting the composition obtained in step S6 to sterilization and/or preservative treatment.

The sterilization may be one of high-temperature sterilization and moist-heat sterilization. The composition is applicable to the field of biomedicines through different carriers.

A preservative used for the preservative treatment may be one of benzoic acid and benzoate, potassium sorbate, sodium dehydroacetate (SDHA), and sodium diacetate (SDA), or a combination of two or more thereof, or an alcohol component with a preservative effect, which is applicable to food, beverage, and health products; and the preservative may be added at an amount 0.01% to 50% of the total amount of the filtrate.

More preferably, the alcohol component with a preservative effect may include one of butanediol, 1,2-hexanediol, and glycerol, or a combination of two or more thereof, which is applicable to cosmetics.

The present invention also provides use of a composition prepared by the method described above in foods, drugs, and cosmetics.

The composition prepared in the present invention, when used in cosmetics, can enhance the inhibition of inflammation, thus relieving skin sensitivity; can also repair cell damage so as to achieve the effect of improving skin cell vitality; can also promote the cell gene expression to repair a skin barrier, thus reducing skin diseases caused by external stimuli.

Compared with the prior art, the present invention has the following beneficial effects.

1) In the present invention, the three medicinal materials (*Sophora flavescens* roots, *Glycyrrhiza inflata* roots, and *Scutellaria baicalensis* roots) are fed in sequence for co-extraction, so that the active ingredients of the three medicinal materials promote each other's extraction efficiency and stability during the whole extraction process. Compared with the method of subjecting each of the medicinal materials to extraction alone and the method of subjecting any two of the medicinal materials to extraction, the present invention requires less process steps, reduced energy consumption, low cost, and simple operations, and thus is suitable for continuous and large-scale production. The method of the present invention is an environmentally-friendly, promising extraction technology for biologically active ingredients, and is suitable for industrialized production.

2) In the present invention, the three medicinal materials (*Sophora flavescens* roots, *Glycyrrhiza inflata* roots, and *Scutellaria baicalensis* roots) are fed in sequence for co-extraction, which improves the extraction efficiency of active ingredients and shortens a process. Therefore, a process can be completed in a short time to reduce the risk that water-soluble samples are contaminated by bacteria due to long-time production, which is conducive to the use and preservation of products.

3) The present invention does not use organic solvents in the process of extraction, separation, and purification, so that the solvent residues in medicines, health products, foods, and cosmetics are reduced, which is beneficial to the widespread use of products; and the recovery, storage, and discharge of organic solvents are reduced, which is beneficial to the use of factory production equipment and facilitates environmental protection and energy conservation.

4) In addition to the necessary washing wastewater generated during the preparation process, all solvents used in the process serve as solvents for products, and no other wastewater is generated, which is energy saving and environmentally friendly.

5) Through the above-mentioned method where the three medicinal materials (*Sophora flavescens* roots, *Glycyrrhiza inflata* roots, and *Scutellaria baicalensis* roots) are fed in sequence for co-extraction in the present invention, contents of biologically active ingredients are increased, and the ingredients are more stable in a solution due to mutual promotion of molecules, making a final product have improved and expanded efficacy.

DETAILED DESCRIPTION OF THE EMBODIMENTS

Figure 1:
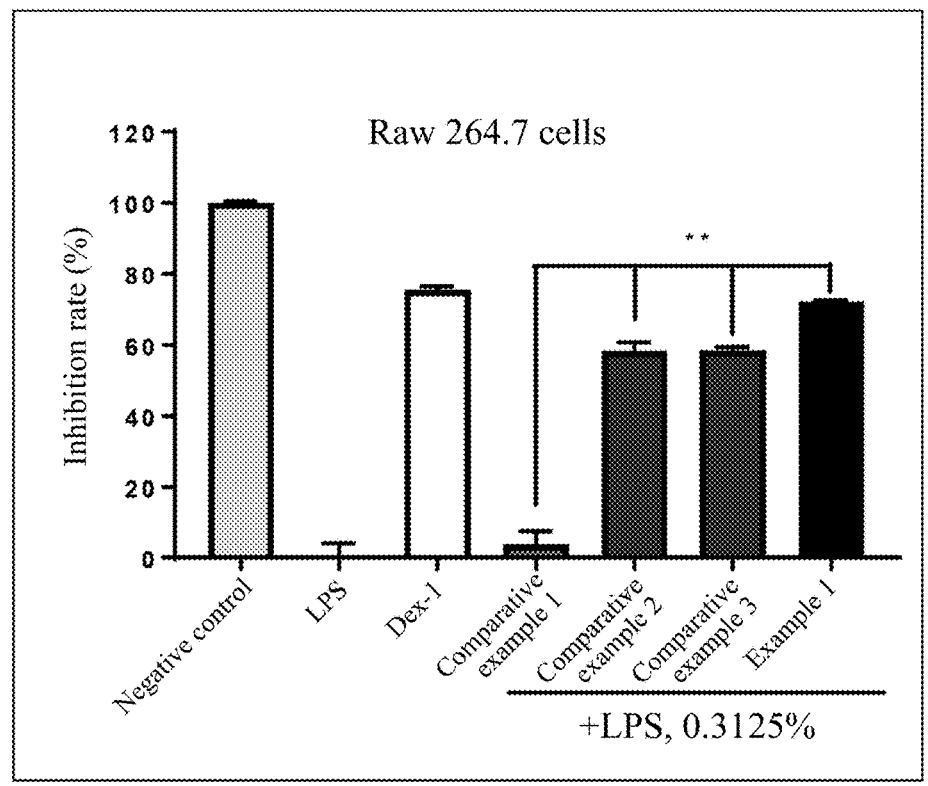
FIG. 1 is a diagram showing inhibition rates of different test substance samples at a concentration of 0.3125%.

The present invention is described in detail below with reference to specific examples. The following examples will help those skilled in the art to further understand the present invention, but do not limit the present invention in any way. It should be noted that those of ordinary skill in the art can further make several variations and improvements without departing from the idea of the present invention. These all fall within the protection scope of the present invention.

Example 1

An environmentally-friendly preparation method of a composition containing anti-inflammatory active ingredients included the following steps:

(1) 1,000 g of water was weighed and added to an extracting tank, a pH was adjusted to 4.5 with dilute HCl, and a resulting solution was heated to 80° C.; and then 40 g of *Sophora flavescens* roots was weighed and added to the extracting tank, and extraction was conducted for 2 h at 80° C.;

(2) 10% NaOH was added to a solution obtained in step (1) to adjust a pH to 10, and then 40 g of *Glycyrrhiza inflata* roots was added; and a resulting mixture was heated to boiling, and extraction was conducted for 30 min;

(3) 40 g of *Scutellaria baicalensis* roots was added to a solution obtained in step (2), and extraction was conducted for 2 h; and a resulting solution was filtered to obtain a filtrate, and a pH of the filtrate was adjusted to 7.5;

(4) 1% activated carbon was added to the filtrate obtained in step (3), and a resulting mixture was heated to 95° C.; reaction was conducted at the temperature for 1 h; and a resulting reaction solution was filtered to obtain a filtrate;

(5) a 5% ZTC clarifying agent II was added to the filtrate obtained in step (4), and a resulting mixture stood for 1 h and filtered;

(6) a filtrate obtained in step (5) was filtered through a microfiltration membrane to remove suspended solids, bacteria, etc., then through an ultrafiltration membrane to remove macromolecular organics, proteins, etc., and finally through an RO membrane for desalination to obtain a filtrate;

(7) butanediol was added to the filtrate obtained in step (6) to obtain a light-yellow transparent liquid with a butanediol content of 35%, namely, the composition.

In the obtained composition, matrine has an extraction yield of 95%, glycyrrhizic acid in *Glycyrrhiza inflata* has an extraction yield of 94%, and baicalin has an extraction yield of 91%.

Example 2

An environmentally-friendly preparation method of a composition containing anti-inflammatory active ingredients included the following steps:

(1) 1,000 g of water was weighed and added to an extracting tank, a pH was adjusted to 4 with dilute HCl, and a resulting solution was heated to 70° C.; and then 30 g of *Sophora flavescens* roots was weighed and added to the extracting tank, and extraction was conducted for 1 h at 70° C.;

(2) 10% NaOH was added to a solution obtained in step (1) to adjust a pH to 9, and then 40 g of *Glycyrrhiza inflata* roots was added; and a resulting mixture was heated to boiling, and extraction was conducted for 60 min;

(3) 30 g of *Scutellaria baicalensis* roots was added to a solution obtained in step (2), and extraction was conducted for 1 h; and a resulting solution was filtered to obtain a filtrate, and a pH of the filtrate was adjusted to 6.5;

(4) 0.5% activated carbon was added to the filtrate obtained in step (3), and a resulting mixture was heated to 90° C.; reaction was conducted at the temperature for 45 min; and a resulting reaction solution was filtered to obtain a filtrate;

(5) a 0.5% chitosan clarifying agent was added to the filtrate obtained in step (4), and a resulting mixture stood for 45 min and filtered;

(6) a filtrate obtained in step (5) was filtered through a microfiltration membrane to remove suspended solids, bacteria, etc., then through an ultrafiltration membrane to remove macromolecular organics, proteins, etc., and finally through an RO membrane for desalination to obtain a filtrate;

(7) butanediol was added to the filtrate obtained in step (6) to obtain a light-yellow transparent liquid with a butanediol content of 35%, namely, the composition.

In the obtained composition, matrine has an extraction yield of 96%, glycyrrhizic acid in *Glycyrrhiza inflata* has an extraction yield of 96%, and baicalin has an extraction yield of 93%.

Example 3

An environmentally-friendly preparation method of a composition containing anti-inflammatory active ingredients included the following steps:

(1) 1,000 g of water was weighed and added to an extracting tank, a pH was adjusted to 3 with dilute HCl, and a resulting solution was heated to 60° C.; and then 21 g of *Sophora flavescens* roots was weighed and added to the extracting tank, and extraction was conducted for 30 min at 60° C.;

(2) 1% NaOH was added to a solution obtained in step (1) to adjust a pH to 8, and then 21 g of *Glycyrrhiza inflata* roots was added; and a resulting mixture was heated to boiling, and extraction was conducted for 120 min;

(3) 21 g of *Scutellaria baicalensis* roots was added to a solution obtained in step (2), and extraction was conducted for 30 min; and a resulting solution was filtered to obtain a filtrate, and a pH of the filtrate was adjusted to 5.5;

(4) 0.2% activated carbon was added to the filtrate obtained in step (3), and a resulting mixture was heated to 85° C.; reaction was conducted at the temperature for 0.5 h; and a resulting reaction solution was filtered to obtain a filtrate;

(5) a 1% ZTC clarifying agent II was added to the filtrate obtained in step (4), and a resulting mixture stood for 0.5 h and filtered;

(6) a filtrate obtained in step (5) was filtered through a microfiltration membrane to remove suspended solids, bacteria, etc., then through an ultrafiltration membrane to remove macromolecular organics, proteins, etc., and finally through an RO membrane for desalination to obtain a filtrate;

(7) butanediol was added to the filtrate obtained in step (6) to obtain a light-yellow transparent liquid with a butanediol content of 35%, namely, the composition.

In the obtained composition, matrine has an extraction yield of 96%, glycyrrhizic acid in *Glycyrrhiza inflata* has an extraction yield of 97%, and baicalin has an extraction yield of 94%.

Comparative Example 1

30 g of *Sophora flavescens* roots and 40 g of *Glycyrrhiza inflata* roots were simultaneously fed, and then extraction was conducted with water at 80° C. for 2 h to obtain a filtrate 1. 30 g of *Scutellaria baicalensis* roots alone was subjected to extraction at 80° C. for 2 h to obtain a filtrate 2. The filtrate 1 and the filtrate 2 were mixed, and a resulting mixture was subjected to the treatments of steps (4) to (7) in Example 1 to obtain a composition.

Comparative Example 2

30 g of *Scutellaria baicalensis* roots and 40 g of *Glycyrrhiza inflata* roots were simultaneously fed and then extraction was conducted with water at 80° C. for 2 h to obtain a filtrate 1. 30 g of *Sophora flavescens* roots alone was subjected to extraction at 80° C. for 2 h to obtain a filtrate 2. The filtrate 1 and the filtrate 2 were mixed, and a resulting mixture was subjected to the treatments of steps (4) to (7) in Example 1 to obtain a composition.

Comparative Example 3

30 g of *Scutellaria baicalensis* roots and 30 g of *Sophora flavescens* roots were simultaneously fed and then extraction was conducted with water at 80° C. for 2 h to obtain a filtrate 1. 30 g of *Glycyrrhiza inflata* roots alone was subjected to extraction at 80° C. for 2 h to obtain a filtrate 2. The filtrate 1 and the filtrate 2 were mixed, and a resulting mixture was subjected to the treatments of steps (4) to (7) in Example 1 to obtain a composition.

Effect Verification:

The composition solutions obtained in Example 1 and Comparative Examples 1, 2, and 3 were tested for efficacy on skin-related cells. Specific results were as follows.

1. Cytotoxicity

Cytotoxicity refers to a deleterious effect on cell structure and/or basic processes of cell survival, proliferation and function. Toxicity is a result of non-specific changes in basic cell functions (such as mitochondria, lysosomes, and plasma membrane integrity), which may eventually lead to changes in organ-specific functions or death of an organism.

The mouse macrophage cell line Raw 264.7 has strong ability to adhere and swallow antigens, which is a cell line commonly used for the study of microbiology and immunology and is also one of the most classic cell lines for the study of anti-inflammatory effects. Neutral red (NR) is a weakly-cationic in vitro reactive dye, which easily diffuses through the plasma membrane and accumulates in the lysosome, and combines with the anionic lysosome matrix to form an electronically-stable state. Toxic substances change a cell surface or lysosomal membrane, causing lysosomal fragility and other harmful changes that are gradually irreversible. These harmful changes can cause cell death and/or inhibit cell growth, thereby leading to a decrease in the amount of NR stored in cells. Therefore, NR uptake experiments can reflect cytotoxicity.

In this experiment, the toxicity of the compositions obtained in the examples and comparative examples to Raw 264.7 cells was first studied to evaluate the safety of the compositions. Main reagents and instruments used in the experiment were shown in Table 1. Raw264.7 cells were used for the NR uptake experiment.

TABLE 1

Main reagents and instruments used in the experiment

| Name of instruments and reagents | Brand | Model |
|---|---|---|
| Raw264.7 cell | ATCC | TIB-71 |
| DMEM medium | Gibco | 10569-010 |

TABLE 1-continued

Main reagents and instruments used in the experiment

| Name of instruments and reagents | Brand | Model |
|---|---|---|
| Fetal bovine serum (FBS) | Corning | 35-076-CV |
| Penicillin/streptomycin (PS) | Corning | 15140-122 |
| 0.25% trypsin | Gibco | 25200-056 |
| Phosphate-buffered saline (PBS) | Sigma | P4417-50TAB |
| NR dye | Sigma | N7005-1G |
| Inverted microscope | Jiangnan Yongxing | XD202 |
| Cell counter | Thermo | Countess II |
| 96-well plate | Corning | 3599 |
| Carbon dioxide incubator | Thermo | 371 |
| Microplate shaker | Kylin-bell | QB9001 |
| Microplate reader | Thermo | MultiSkan FC |

Raw264.7 cells at logarithmic growth phase were collected as follows: culture medium was discarded, and the cells were washed twice with PBS, added with 0.25% trypsin, and placed at 37° C. for 5 min; digestion was terminated with DMEM complete culture medium including 10% FBS and 1% PS, and a resulting solution was centrifuged at 1,000 rpm for 3 mi; and a resulting supernatant was discarded, and obtained cells were resuspended in complete culture medium and counted. A cell concentration was adjusted to $5\times10^5$ cells/ml, and a resulting cell suspension was added to a 96-well plate at 100 μl/well. After the cells grew adherently 24 h later, 100 μl of each of test substance samples with different concentrations was added to each well. A resulting mixture was thoroughly mixed and incubated for 24±1 h in an incubator.

Experimental groups were shown in Table 2 below:

TABLE 2

| Group name | Sample treatment |
|---|---|
| Blank control group | Complete culture medium |
| Negative control group | Complete culture medium + Raw264.7 cells |
| Test substance group | Complete culture medium + Raw264.7 cells + test substance |

Notes:
The test substances were composition solutions of different concentrations obtained by diluting the compositions prepared in Examples 1 to 3 and Comparative Examples 1 to 3 (starting from a concentration of 5%, 4-fold dilution was adopted to obtain final concentrations: 5%, 1.25%, 0.3125%, and 0.078%).

After the treatment, the culture medium was discarded, 200 μl of an NR staining solution (33 μg/ml) was added to each well, and the plate was placed in an incubator for 3±0.1 h. A resulting supernatant was discarded (no residue), 150 μl of an NR eluent (1% glacial acetic acid+50% absolute ethanol+4900 ultrapure water) was added to each well, and the plate was shaken at room temperature for 20 min to 45 min in the dark. An absorbance (A) was determined at 540 nm with a microplate reader, and a cell viability was calculated. Cell viability $(0\%) = A_{test\ substance\ group}/A_{negative\ control} \times 100\%$ As shown in Table 3, after Raw 264.7 cells were treated for 24 h with composition solutions at a concentration of 1.25% obtained by diluting the compositions prepared in examples and comparative examples, except for Comparative Example 1, the cell viability in the remaining groups decreased to 60% or lower, indicating that the compositions exhibited a specified toxic effect on cells at a high concentration. After the cells were treated with each composition at a concentration of 10.3125, the cell activity in each example was significantly higher than that in the 3 comparative examples, indicating that the cytotoxicity of the examples was relatively low.

TABLE 3

Effects of compositions at different concentrations on cell viability

| Sample treatment | Concentration 1 (%) | Cell viability 1 (%) | Concentration 2 (%) | Cell viability 2 (%) |
|---|---|---|---|---|
| Negative control group | — | 100.00 | — | 100.00 |
| Comparative Example 1 | 1.25 | 104.92 | 0.3125 | 100.73 |
| Comparative Example 2 | 1.25 | 21.30 | 0.3125 | 32.48 |
| Comparative Example 3 | 1.25 | 20.78 | 0.3125 | 31.10 |
| Example 1 | 1.25 | 13.69 | 0.3125 | 116.20 |
| Example 2 | 1.25 | 32.59 | 0.3175 | 108.44 |
| Example 3 | 1.25 | 55.34 | 0.3175 | 106.31 |

2. Anti-Inflammatory Effect

Inflammation refers to a basic pathological process (mainly defensive response) of a living tissue with a vascular system to the stimulation of various damage factors. The clinical manifestations of inflammation include a series of phenomena such as redness, swelling, fever, itching, and pain.

Lipopolysaccharide (LPS) is one of the main components in the cell wall of Gram-negative bacilli and is also one of the main substances that induce inflammation. In an inflammatory response process, macrophages indirectly or directly participate in response processes of various inflammatory diseases by generating a variety of different cytokines or releasing lysosomal enzymes, and can respond to the stimulation of extracellular LPS and initiate a series of cascade reactions in cells caused by the activation of corresponding signal proteins to produce various inflammatory mediators, such as prostaglandin E2 (PGE-2) and nitric oxide (NO).

In this experiment, Raw 264.7 cells were stimulated by LPS, then cell culture was collected, and the expression of the inflammatory factor PGE-2 was determined by enzyme-linked immunosorbent assay (ELISA). The compositions obtained in the examples and comparative examples were compared in terms of the influence on anti-inflammatory effects. Main reagents and instruments used in the experiment were shown in Table 4. Raw264.7 cells and LPS were used for the experiment.

TABLE 4

Main reagents and instruments used in the experiment.

| Name of instruments and reagents | Brand | Model |
|---|---|---|
| Raw264.7 cell | ATCC | TIB-71 |
| DMEM medium | Gibco | 10569-010 |
| FBS | Corning | 35-076-CV |
| PS | Corning | 15140-122 |
| 0.25% trypsin | Gibco | 25200-056 |
| PBS | Sigma | P4417-50TAB |
| LPS | Sigma | L3012-10MG |
| Dexamethasone (Dex) | Sigma | D4902-25MG |
| PGE-2 ELISA kit | Cayman | 514010 |
| Inverted microscope | Jiangnan Yongxing | XD202 |
| Cell counter | Thermo | Countess II |
| 96-well plate | Corning | 3599 |
| Carbon dioxide incubator | Thermo | 371 |
| Microplate shaker | Kylin-bell | QB9001 |
| Microplate reader | Thermo | MultiSkan FC |

Raw264.7 cells at logarithmic growth phase were collected as follows: culture medium was discarded, and the cells were washed twice with PBS, added with 0.25% trypsin, and placed at 37° C. for 5 min; digestion was terminated with DMEM complete culture medium including 10% FBS and 1% PS, and a resulting solution was centrifuged at 1,000 rpm for 3 min; and a resulting supernatant was discarded, and obtained cells were resuspended in complete culture medium and counted. A cell concentration was adjusted to $5 \times 10^5$ cells/ml, and a resulting cell suspension was added to a 96-well plate at 100 l/well. After the cells grew adherently 24 h later, 100 μl of each of test substance samples with different concentrations, positive control, negative control, and 1 μg/ml LPS were added to each well. A resulting mixture was thoroughly mixed and incubated for 24 h±1 h in an incubator. According to cytotoxicity results, a concentration (less than 0.3125%) that shows little effect on cell activity was selected for the verification of the anti-inflammatory experiment. Experimental groups were shown in Table 5 below:

TABLE 5

| Group name | Sample treatment |
|---|---|
| Blank control group | Complete culture medium |
| Negative control group | Complete culture medium + Raw264.7 cells |
| LPS group (model group) | Complete culture medium + Raw264.7 cells + LPS |
| Positive control group | Complete culture medium + Raw264.7 cells + LPS + Dex |
| Test substance group | Complete culture medium + Raw264.7 cells + LPS + test substance |

Notes:
The test substances were composition solutions of different concentrations (0.3125% and 0.078%) obtained by diluting the compositions prepared in Example 1 and Comparative Examples 1 to 3. Dex refers to dexamethasone (10 μM).

After the treatment, cell culture was collected to a new 96-well plate, and the expression of PGE-2 was determined by ELISA according to instructions of a kit. A PGE-2 content (E) was calculated according to a standard curve, and relative to the LPS group, a relative inhibition rate was calculated for each sample (inhibition rate (%)= $(1 - E_{test\ substance\ group}/E_{LPS\ group}) \times 100$).

Figure 2:
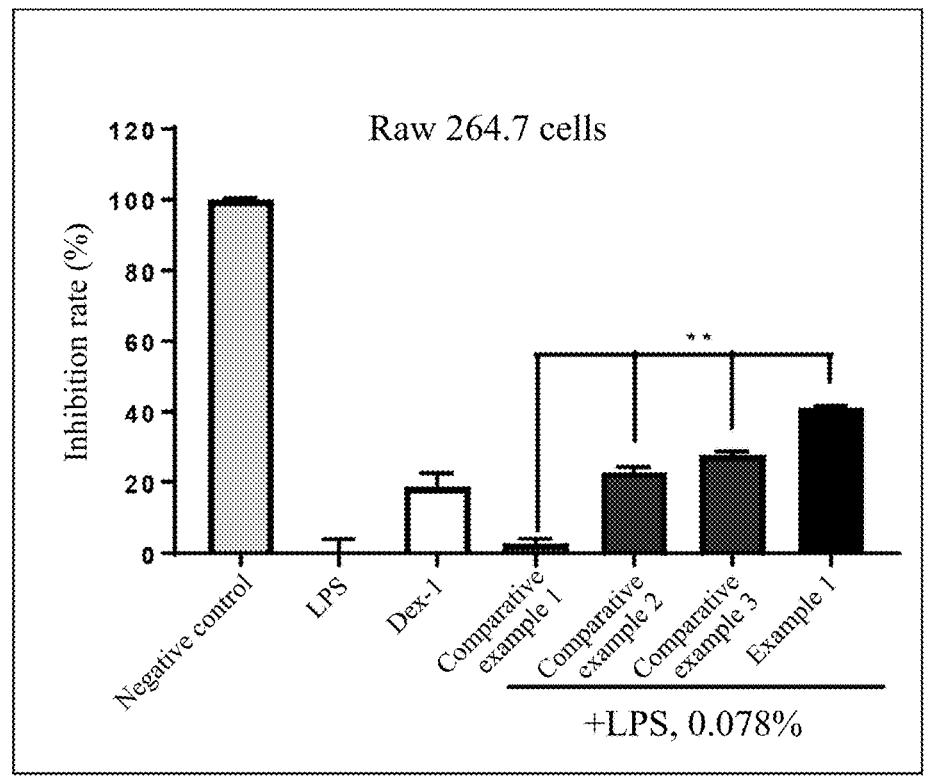
FIG. 2 is a diagram showing inhibition rates of different test substance samples at a concentration of 0.078%.

As shown in FIG. 1 and FIG. 2, on Raw 264.7 cells, LPS significantly induces the expression of PGE-2. The positive control Dex can inhibit the expression of PGE-2 in a dose-dependent manner, and can achieve an inhibition rate reaching 75.27% at 10 μM (Dex-10 group shown in FIG. 1). A liquid plant extract composition prepared in Example 1 can reduce the expression of PGE-2 in a dose-dependent manner in a range of 0.078% to 0.3125%, exhibiting a statistically significant difference from the 3 comparative examples (**$P<0.01$). The composition can achieve an inhibition rate of 72.00% at a concentration of 0.3125% and an inhibition rate of 41.17% at a concentration of 0.078%, which is equivalent to the anti-inflammatory effect of the positive control Dex.

In summary, compared with Comparative Examples 1 to 3, the composition prepared in Example 1 shows a lower toxicity to mouse macrophage cells Raw 264.7 and a stronger inhibitory effect on the expression of the inflammatory factor PGE-2 induced by LPS.

As determined, the compositions prepared in Examples 2 and 3 also show a low toxicity to mouse macrophage cells Raw 264.7 and a strong inhibitory effect on the expression of the inflammatory factor PGE-2 induced by LPS.

There are many ways to specifically apply the present invention, and the above are merely preferred implementations of the present invention. It should be noted that the foregoing examples are provided only for illustrating the present invention and are not intended to limit the protection scope of the present invention. For a person of ordinary skill in the art, several improvements may further be made without departing from the principle of the present invention, and these improvements should also be considered as falling within the protection scope of the present invention.

What is claimed is:

1. An environmentally-friendly preparation method of a composition containing anti-inflammatory active ingredients, comprising the following steps:
    S1. weighing a predetermined volume of water and adjusting a pH of the predetermined volume of water, adding *Sophora flavescens* roots to obtain a first resulting mixture, and subjecting the first resulting mixture to a first extraction at a predetermined temperature to obtain an extracted solution;
    S2. adjusting a pH of the extracted solution obtained in step S1, adding *Glycyrrhiza inflata* roots to obtain a second resulting mixture, and heating the second resulting mixture to boiling for a second extraction to obtain an extracted boiling solution;
    S3. adding *Scutellaria baicalensis* roots to the extracted boiling solution obtained in step S2 to obtain a third resulting mixture, and subjecting the third resulting mixture to a third extraction, a first filtration, and a pH adjustment to obtain a first filtrate;
    S4. adding activated carbon to the first filtrate obtained in step S3 to obtain a fourth resulting mixture, and subjecting the fourth resulting mixture to an incubation and a second filtration to obtain a second filtrate;
    S5. adding a clarifying agent to the second filtrate obtained in step S4 to obtain a fifth resulting mixture, and subjecting the fifth resulting mixture to a standing and a third filtration to obtain a third filtrate; and
    S6. subjecting the third filtrate obtained in step S5 to a membrane separation to obtain the composition containing the anti-inflammatory active ingredients.

2. The environmentally-friendly preparation method according to claim 1, wherein, the *Scutellaria baicalensis* roots, the *Sophora flavescens* roots, and the *Glycyrrhiza inflata* roots are added at a ratio of (21-40):(21-40):(21-40).

3. The environmentally-friendly preparation method according to claim 1, wherein, in step S1, the predetermined volume of water is added at an amount 5 to 10 times a total amount of the *Scutellaria baicalensis* roots, the *Sophora flavescens* roots and the *Glycyrrhiza inflata* roots; the pH of the predetermined volume of water is 3.0 to 7.0; and the first extraction is conducted at the predetermined temperature of 60° C. to 80° C. for 30 min to 2 h.

4. The environmentally-friendly preparation method according to claim 1, wherein, in step S2, the pH of the extracted solution is adjusted to 8 to 10 with 1% to 10% NaOH, and the second resulting mixture is subjected to the second extraction for 30 min to 2 h.

5. The environmentally-friendly preparation method according to claim 1, wherein, in step S3, the third extraction is conducted for 30 min to 2 h, and a pH of the third resulting mixture is adjusted to 5.5 to 7.5.

6. The environmentally-friendly preparation method according to claim 1, wherein, in step S4, the activated carbon is added at an amount 0.2% to 1% of a total amount of the first filtrate; and the incubation is conducted at 85° C. to 95° C. for 0.5 h to 1 h.

7. The environmentally-friendly preparation method according to claim 1, wherein, in step S5, the clarifying agent is at least one selected from the group consisting of chitosan, ZTC clarifying agent I-IV, and 101 juice clarifying agent; the clarifying agent is added at an amount 1% to 5% of a total amount of the second filtrate; and the standing lasts for 0.5 h to 1 h.

8. The environmentally-friendly preparation method according to claim 1, wherein, in step S6, the membrane separation comprises: separating with a microfiltration membrane; separating and concentrating with an ultrafiltration membrane; and desalting with a reverse osmosis (RO) membrane.

9. The environmentally-friendly preparation method according to claim 1, wherein, the environmentally-friendly preparation method further comprises the step of subjecting the composition containing the anti-inflammatory active ingredients obtained in step S6 to a sterilization and/or a preservative treatment;
    the sterilization is one of a high-temperature sterilization and a moist-heat sterilization; and
    a preservative used for the preservative treatment is at least one selected from the group consisting of benzoic acid and benzoate, potassium sorbate, sodium dehydroacetate (SDHA), and sodium diacetate (SDA), or the preservative is an alcohol component with a preservative effect; and the preservative is added at an amount 0.01% to 50% of a total amount of the third filtrate.

10. A method of using the composition containing the anti-inflammatory active ingredients prepared by the environmentally-friendly preparation method according to claim 1, comprising using the composition containing the anti-inflammatory active ingredients in health foods, drugs, and cosmetics.

* * * * *